United States Patent
Stevenson et al.

(10) Patent No.: US 10,722,384 B2
(45) Date of Patent: Jul. 28, 2020

(54) MEDICAL MATERIAL MIXER AND TRANSFER APPARATUS AND METHOD FOR USING THE SAME

(71) Applicant: NORDSON CORPORATION, Westlake, OH (US)

(72) Inventors: Mark Stevenson, Cottage Grove, MN (US); Jon E. Hoogenakker, Inner Grove Heights, MN (US); Alexander Cromett, St. Paul, MN (US); Zachary Rzeszutek, Champlin, MN (US)

(73) Assignee: Nordson Corporation, Westlake, OH (US)

( * ) Notice: Subject to any disclaimer, the term of this patent is extended or adjusted under 35 U.S.C. 154(b) by 192 days.

(21) Appl. No.: 15/907,083

(22) Filed: Feb. 27, 2018

(65) Prior Publication Data
US 2018/0250145 A1  Sep. 6, 2018

Related U.S. Application Data

(60) Provisional application No. 62/465,251, filed on Mar. 1, 2017.

(51) Int. Cl.
*A61F 2/46* (2006.01)
*A61B 17/88* (2006.01)
(Continued)

(52) U.S. Cl.
CPC ........ *A61F 2/4644* (2013.01); *A61B 17/8833* (2013.01); *A61B 2017/8838* (2013.01);
(Continued)

(58) Field of Classification Search
CPC ........... A61F 2/4644; A61F 2002/4645; A61B 17/8833; A61B 2017/8838;
(Continued)

(56) References Cited

U.S. PATENT DOCUMENTS

| 3,317,274 A * | 5/1967 | McCormick | G01K 1/083 |
| | | | 206/212 |
| 4,277,184 A * | 7/1981 | Solomon | A61B 17/8822 |
| | | | 366/139 |

(Continued)

FOREIGN PATENT DOCUMENTS

| CH | 708198 A1 | 12/2014 |
| CN | 202723953 U | 2/2013 |

(Continued)

OTHER PUBLICATIONS

ISA/220—Notification of Transmittal of Search Report and Written Opinion of the ISA dated Jun. 8, 2018 for WO Application No. PCT/US18/020230.

*Primary Examiner* — Tony G Soohoo
(74) *Attorney, Agent, or Firm* — Baker & Hostetler LLP

(57) ABSTRACT

Methods, apparatus and kits for preparing a medical mixture are disclosed. A method of preparing the medical mixture includes introducing a material into a tray, transferring the material from the tray to a scooper, releasably securing the scooper to the tray, and introducing a tubular member defining a lumen into the scooper such that the material within the scooper enters the lumen. A mixing apparatus includes a tray comprising a body defining a mixing receptacle configured to receive a material, a scooper having a proximal end with a proximal opening and a distal end with a distal opening, and a connector configured to releasably secure the scooper to the tray. A kit includes a tubular member, a stylet, a tray, and a scooper.

13 Claims, 15 Drawing Sheets

(51) Int. Cl.
*A61L 27/36* (2006.01)
*B01F 15/02* (2006.01)

(52) U.S. Cl.
CPC ... *A61F 2002/4645* (2013.01); *A61L 27/3608* (2013.01); *A61L 2430/02* (2013.01); *B01F 15/0274* (2013.01); *B01F 2215/0029* (2013.01)

(58) Field of Classification Search
CPC ............ A61L 27/3608; A61L 2430/02; B01F 2215/0029; B01F 15/0274
See application file for complete search history.

(56) References Cited

U.S. PATENT DOCUMENTS

| | | | | |
|---|---|---|---|---|
| 4,294,349 A * | 10/1981 | Ibsen | A61C 19/005 | 206/523 |
| 4,420,085 A * | 12/1983 | Wilson | A61M 5/002 | 206/370 |
| 4,761,379 A * | 8/1988 | Williams | A61B 10/0051 | 206/569 |
| 4,844,249 A * | 7/1989 | Coulombe | A61M 5/3205 | 206/438 |
| 4,852,584 A * | 8/1989 | Selby | B01L 3/00 | 600/573 |
| 4,961,500 A * | 10/1990 | Coulombe | A61M 5/008 | 206/232 |
| 4,997,084 A * | 3/1991 | Opie | A61B 1/00142 | 206/364 |
| 5,007,535 A * | 4/1991 | Meseke | A61M 5/008 | 206/363 |
| 5,024,326 A * | 6/1991 | Sandel | A61B 50/3001 | 206/363 |
| 5,201,418 A * | 4/1993 | Hanlon | A61M 5/3205 | 206/366 |
| 5,203,459 A * | 4/1993 | Wade | A47G 21/004 | 206/572 |
| 5,240,415 A * | 8/1993 | Haynie | A61C 19/066 | 433/216 |
| 5,449,071 A * | 9/1995 | Levy | A61B 10/0096 | 206/569 |
| 5,586,821 A * | 12/1996 | Bonitati | A61B 17/8825 | 366/139 |
| 5,868,250 A * | 2/1999 | Brackett | A61M 5/008 | 206/363 |
| 5,975,305 A * | 11/1999 | Barger | A61J 7/0023 | 206/572 |
| 6,364,519 B1 * | 4/2002 | Hughes | A61B 17/8833 | 220/221 |
| 6,435,705 B1 | 8/2002 | Long | | |
| 6,458,147 B1 * | 10/2002 | Cruise | B01F 13/0023 | 606/214 |
| 6,536,937 B1 * | 3/2003 | Burchett | B01F 13/002 | 366/139 |
| 6,588,587 B2 * | 7/2003 | Johnson | B25H 3/021 | 206/363 |
| 6,779,657 B2 * | 8/2004 | Mainwaring | B65D 25/08 | 206/15.3 |
| D500,850 S * | 1/2005 | Clark | G01F 19/002 | D24/116 |
| 6,880,590 B2 | 4/2005 | Cornfield | | |
| 6,957,909 B1 * | 10/2005 | Dingeldein | B65D 75/36 | 220/221 |
| 7,160,020 B2 * | 1/2007 | Sand | B01F 7/0005 | 366/139 |
| 7,278,778 B2 * | 10/2007 | Sand | B01F 7/0005 | 366/139 |
| 7,308,985 B2 * | 12/2007 | Riley | A61J 1/00 | 206/363 |
| 7,331,450 B2 * | 2/2008 | Discko, Jr. | A61C 5/60 | 206/369 |
| D636,890 S * | 4/2011 | Teys | D24/224 | |
| 8,246,572 B2 * | 8/2012 | Cantor | A61F 2/4601 | 604/14 |
| 8,303,599 B2 * | 11/2012 | Hess | A61M 5/008 | 206/219 |
| 8,403,936 B2 * | 3/2013 | Hess | A61M 5/008 | 604/187 |
| 8,408,250 B2 | 4/2013 | McKay | | |
| 8,425,619 B2 * | 4/2013 | Evans | A61L 27/24 | 623/23.51 |
| 8,435,306 B2 * | 5/2013 | Evans | A61L 27/24 | 623/23.51 |
| 8,511,500 B2 * | 8/2013 | Teys | B65D 43/162 | 220/265 |
| 8,673,021 B2 * | 3/2014 | Orr | A61B 17/00234 | 623/23.72 |
| 8,689,972 B2 * | 4/2014 | Sanchez | B65D 75/5866 | 206/219 |
| 8,696,678 B2 | 4/2014 | Foster | | |
| 8,714,354 B2 * | 5/2014 | Cheetham | A61C 5/60 | 206/368 |
| 8,945,134 B2 * | 2/2015 | Hess | A61M 5/008 | 604/187 |
| 9,107,524 B2 * | 8/2015 | Leffler | A61J 7/0023 | |
| 9,114,201 B2 * | 8/2015 | Iio | A61M 5/002 | |
| 9,212,978 B2 * | 12/2015 | Li | C12M 23/42 | |
| 9,283,013 B2 * | 3/2016 | Shimko | A61F 2/28 | |
| 9,345,639 B2 * | 5/2016 | Ferrara | A61J 7/0023 | |
| 9,758,284 B2 * | 9/2017 | Barton | B65D 75/008 | |
| 9,815,606 B2 * | 11/2017 | Barton | B65D 75/5866 | |
| 9,827,111 B2 * | 11/2017 | Orr | A61B 17/00234 | |
| 2002/0191487 A1 * | 12/2002 | Sand | B01F 7/0005 | 366/252 |
| 2004/0010260 A1 * | 1/2004 | Scribner | A61B 17/8833 | 606/93 |
| 2004/0195131 A1 * | 10/2004 | Spolidoro | A61B 50/30 | 206/438 |
| 2004/0238391 A1 * | 12/2004 | Pond | A61C 3/005 | 206/369 |
| 2004/0267277 A1 * | 12/2004 | Zannis | A61F 2/4618 | 606/99 |
| 2005/0011805 A1 * | 1/2005 | Lyons | B44D 2/002 | 206/575 |
| 2005/0034310 A1 | 2/2005 | Conforti | | |
| 2005/0155901 A1 * | 7/2005 | Krueger | A61B 17/8833 | 206/571 |
| 2005/0241965 A1 * | 11/2005 | Kurc | A61B 17/1635 | 206/219 |
| 2008/0033447 A1 * | 2/2008 | Sand | B01F 7/0005 | 606/93 |
| 2008/0045861 A1 * | 2/2008 | Miller | A61B 10/025 | 600/567 |
| 2008/0105328 A1 * | 5/2008 | Desmond | A45C 3/00 | 141/2 |
| 2009/0194446 A1 * | 8/2009 | Miller | A61B 10/025 | 206/438 |
| 2009/0277809 A1 * | 11/2009 | Neidhardt | B65D 1/34 | 206/438 |
| 2009/0283441 A1 * | 11/2009 | Santaw | A45D 40/24 | 206/581 |
| 2011/0071536 A1 * | 3/2011 | Kleiner | A61F 2/4611 | 606/94 |
| 2014/0188001 A1 * | 7/2014 | Miller | A61B 17/162 | 600/567 |
| 2014/0262880 A1 * | 9/2014 | Yoon | A61B 10/025 | 206/363 |
| 2015/0075556 A1 * | 3/2015 | Mortis Simons | A45D 33/24 | 132/294 |
| 2018/0250145 A1 * | 9/2018 | Stevenson | A61F 2/4644 | |

FOREIGN PATENT DOCUMENTS

| | | |
|---|---|---|
| WO | 2004/100741 A1 | 11/2004 |
| WO | 2007/122006 A1 | 11/2007 |
| WO | 2011/159869 A2 | 12/2011 |

* cited by examiner

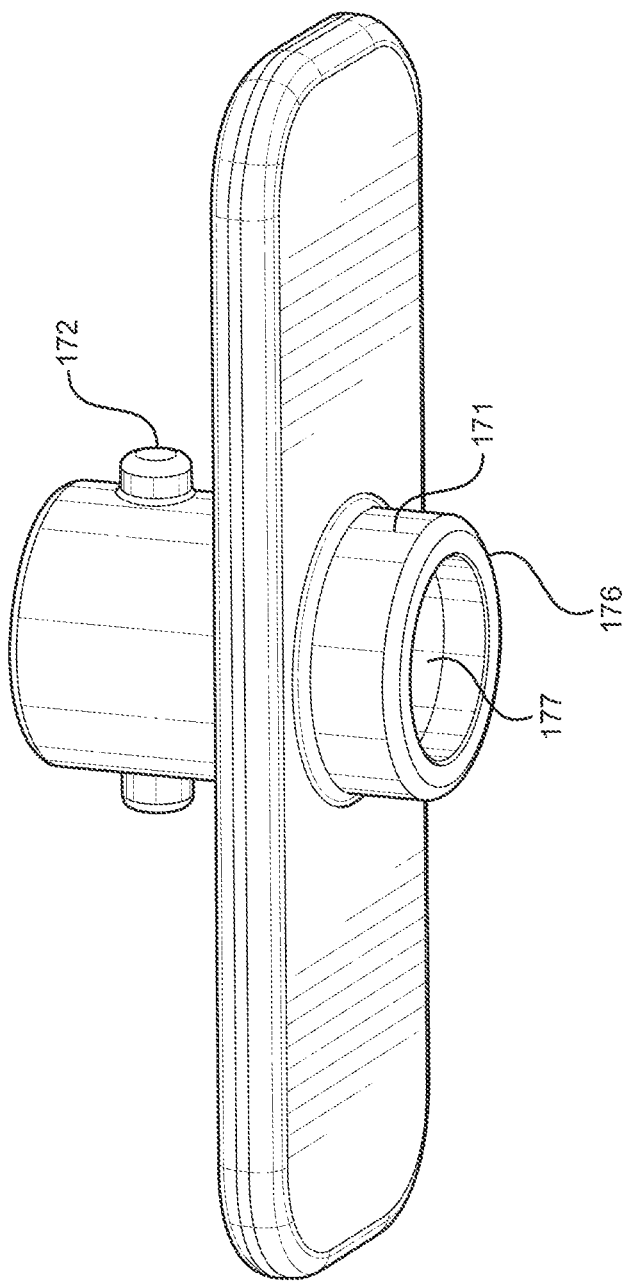

MEDICAL MATERIAL MIXER AND TRANSFER APPARATUS AND METHOD FOR USING THE SAME

CROSS REFERENCE TO RELATED APPLICATIONS

This application claims the benefit of U.S. Provisional Patent App. No. 62/465,251, filed Mar. 1, 2017, the disclosure of which is hereby incorporated by reference herein.

TECHNICAL FIELD

This disclosure is directed to mixing medical material and, more particularly, to an improved mixing apparatus incorporating a mixing tray and a scooper.

BACKGROUND

Bone degradation is a common side effect of various infirmities, injuries and the general aging process. Surgical procedures that seek to alleviate the ailments associated with bone damage are complex and often difficult to perform. A bone graft is a surgical transplant of bone tissue that comes from the patient's body, a donor, or another species to alleviate the ailments of bone degradation. Bone grafts can also be useful for growing new bone tissue around an implanted device, such as a knee replacement.

Materials used in bone grafting are often rough and heterogeneous, making them difficult to prepare, mix and apply. Known methods include preparing and mixing the necessary materials in a mixing bowl and then using a tool, such as a spatula, to transfer the mixed material into a syringe using a funnel. However, it is tedious and time-consuming work to gather the mixed material from the mixing bowl using a spatula, transfer the mixed material to a funnel, and then to transfer the mixed material from the funnel into the syringe using known methods and devices. Moreover, the amount of time required to repeatedly transfer the mixed material, as well as the wasted material resulting from the repeated transfers, increases the cost of a bone grafting procedure.

Therefore, there is a need for improved devices and methods for mixing and transferring a mixed material, such as a bone grafting material.

SUMMARY

A method of preparing a medical mixture includes introducing a material into a tray, transferring the material from the tray to a scooper, releasably securing the scooper to the tray, and introducing a tubular member defining a lumen into the scooper such that the material within the scooper enters the lumen.

Introducing the material may include introducing a first material and a second, different material. The first material may include natural bone and the second material may include synthetic material. The first material and the second material may be mixed in the tray. Introducing material may include introducing the material into a mixing receptacle defined by the tray. The scooper may be releasably secured adjacent the mixing receptacle on the tray. Securing the scooper may include sliding a distal end of the scooper over a post extending from the tray and/or rotating the scooper relative to the post.

A method of preparing a medical mixture according to another embodiment includes introducing a material into a tray, transferring the material from the tray to a scooper having a distal opening at a distal end and a proximal opening at a proximal end, such that the material is transferred to the scooper through the proximal opening, and releasably securing the scooper to a tubular member. The tubular member has a proximal opening at a proximal end and a distal opening at a distal end and defines a lumen that extends from the proximal opening to the distal opening. The distal end of the scooper is releasably secured to the proximal end of the tubular member such that the distal opening of the scooper is in fluid communication with the proximal opening of the tubular member.

Introducing the material may include introducing a first material and a second, different material. The first material may include natural bone and the second material may include synthetic material. A stylet may be moved into the proximal opening of the scooper to push at least some of the material from the scooper into the lumen of the tubular member. The first material and the second material may be mixed in the tray. The material may be introduced into a mixing receptacle defined by the tray. Releasably securing the scooper to the tubular member may include rotating the scooper relative to the tubular member.

A mixing apparatus according to one embodiment includes a tray including a body defining a mixing receptacle configured to receive a material, a scooper having a proximal end with a proximal opening and a distal end with a distal opening, and a connector configured to releasably secure the scooper to the tray.

The mixing receptacle may be concave. The shape of the mixing receptacle may be complementarily to the shape of the proximal end of the scooper, such that the scooper is configured to slide over the mixing receptacle to receive the material. The connector may include a post or a plurality of posts configured to slidably engage with the distal end of the scooper. The distal end of the scooper may define a cavity extending from the proximal opening to the distal opening shaped to receive the post. The post may be cylindrical.

The post may further include a tab extending radially from the post. The distal end of the scooper may define a groove shaped to receive the tab and the groove may spiral at least partially around the circumference of the distal end of the scooper. The tray may be made of polyethylene terephthalate (PET), polypropylene, acrylonitrile butadiene styrene (ABS), or a combination thereof.

A kit for mixing a material according to one embodiment includes a tubular member, a stylet, a tray and a scooper. The tubular member has a proximal opening at a proximal end and a distal opening at a distal end and defines a lumen extending there between. The stylet is configured to slide within the lumen of the tubular member. The tray includes a body defining a concave mixing receptacle and a connector adjacent the mixing receptacle. The scooper includes a proximal opening at a proximal end and a distal opening at a distal end, and defines a cavity extending there between. The proximal end of the scooper has a first shape, and the mixing receptacle has a second shape that complements the first shape of the scooper, such that the scooper is configured to slide over the mixing receptacle to receive the material.

The stylet may be configured to slide into the scooper, pass through the proximal opening and the distal opening of the scooper, and slide into the proximal opening of the tubular member. The connector may include a tab or a plurality of tabs configured to slidably engage with the distal end of the scooper. The tabs may be cylindrical.

The scooper may include a grip configured to receive a finger of a user. The scooper may further define an aperture to the cavity to allow air to move out of the cavity. The tubular member may be at least partially transparent or translucent. The tubular member may include radio-opaque markings. The distal end of the stylet may also include a radio-opaque marking. The tray may be made of polyethylene terephthalate (PET), polypropylene, acrylonitrile butadiene styrene (ABS), or a combination thereof.

Various advantages, features and functions of the present disclosure will become readily apparent and better understood in view of the following description and accompanying drawings. The following description is not intended to limit the scope of the present disclosure, but instead merely details exemplary aspects for ease of understanding.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. In the drawings:

FIG. 13C shows another isometric view of the handle shown in FIG. 13B; and

DETAILED DESCRIPTION

Figure 1:
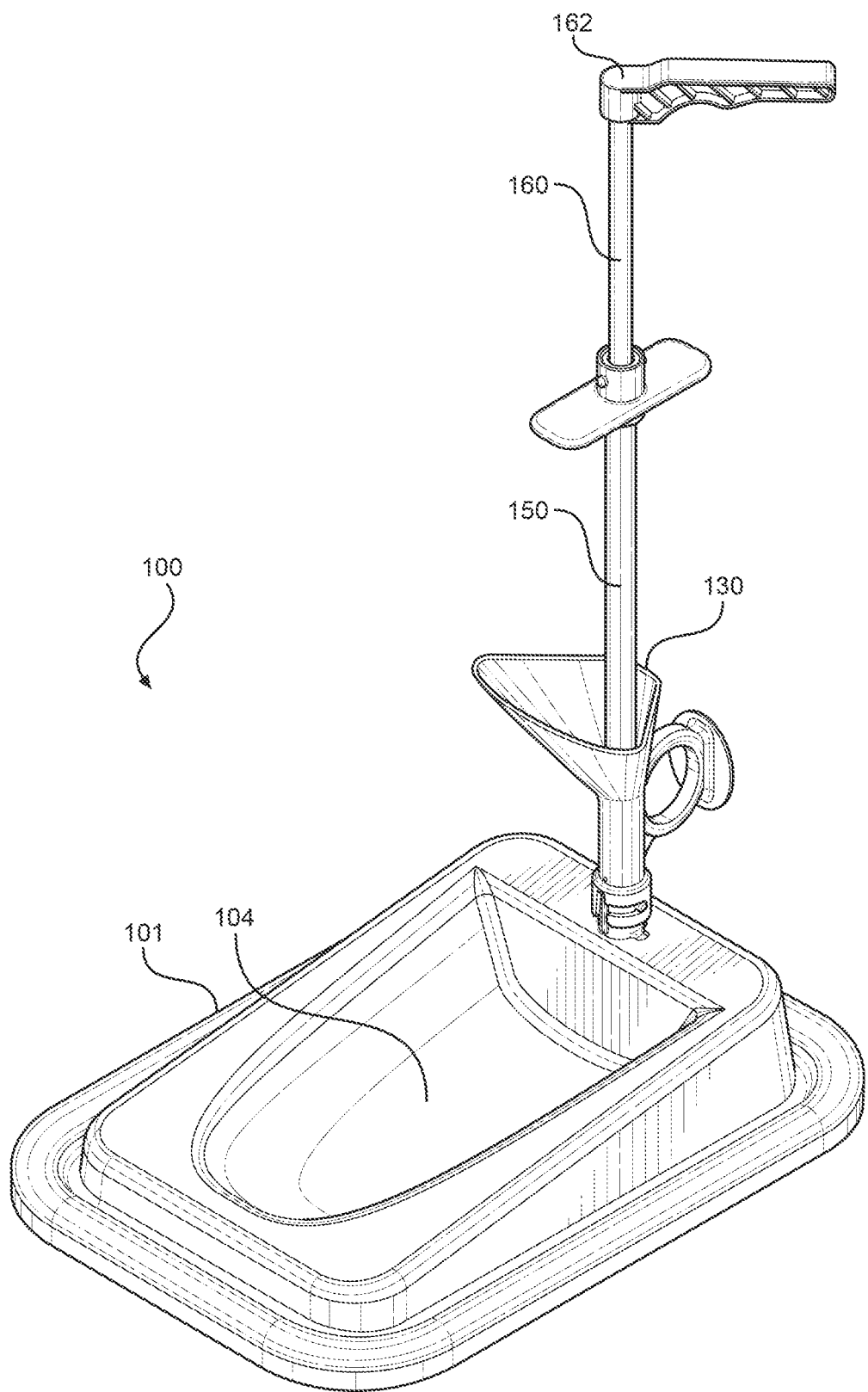
FIG. 1 shows an isometric view of a mixing system according to one embodiment.

A mixing system may be used to prepare materials. The mixing system may be disposable and designed for single use. The mixing system may be used to prepare a single material, or it may be used to prepare and mix multiple materials together. A scooper having a large proximal opening that mates with a mixing tray receives the mixed material. The scooper may then secure to the mixing tray to provide a rigid support for the scooper while a tubular member is inserted into the scooper to receive the mixed material. Alternatively, the scooper may be secured to the tubular member and the mixed material may be pushed into the tubular member. This versatility allows the user to determine how to transfer the mixed material depending on the material characteristics (e.g. viscosity), surgical need, and personal preference with minimal waste of the mixed material.

Certain terminology is used in the description for convenience only and is not limiting. The words "proximal" and "distal" generally refer to positions or directions toward and away from, respectively, an individual using the mixing system. The words "axial", "vertical", "transverse", "left", "right", "above," and "below" designate directions in the drawings to which reference is made. The term "substantially" is intended to mean considerable in extent or largely but not necessarily wholly that which is specified. The terminology includes the above-listed words, derivatives thereof and words of similar import.

Figure 2:
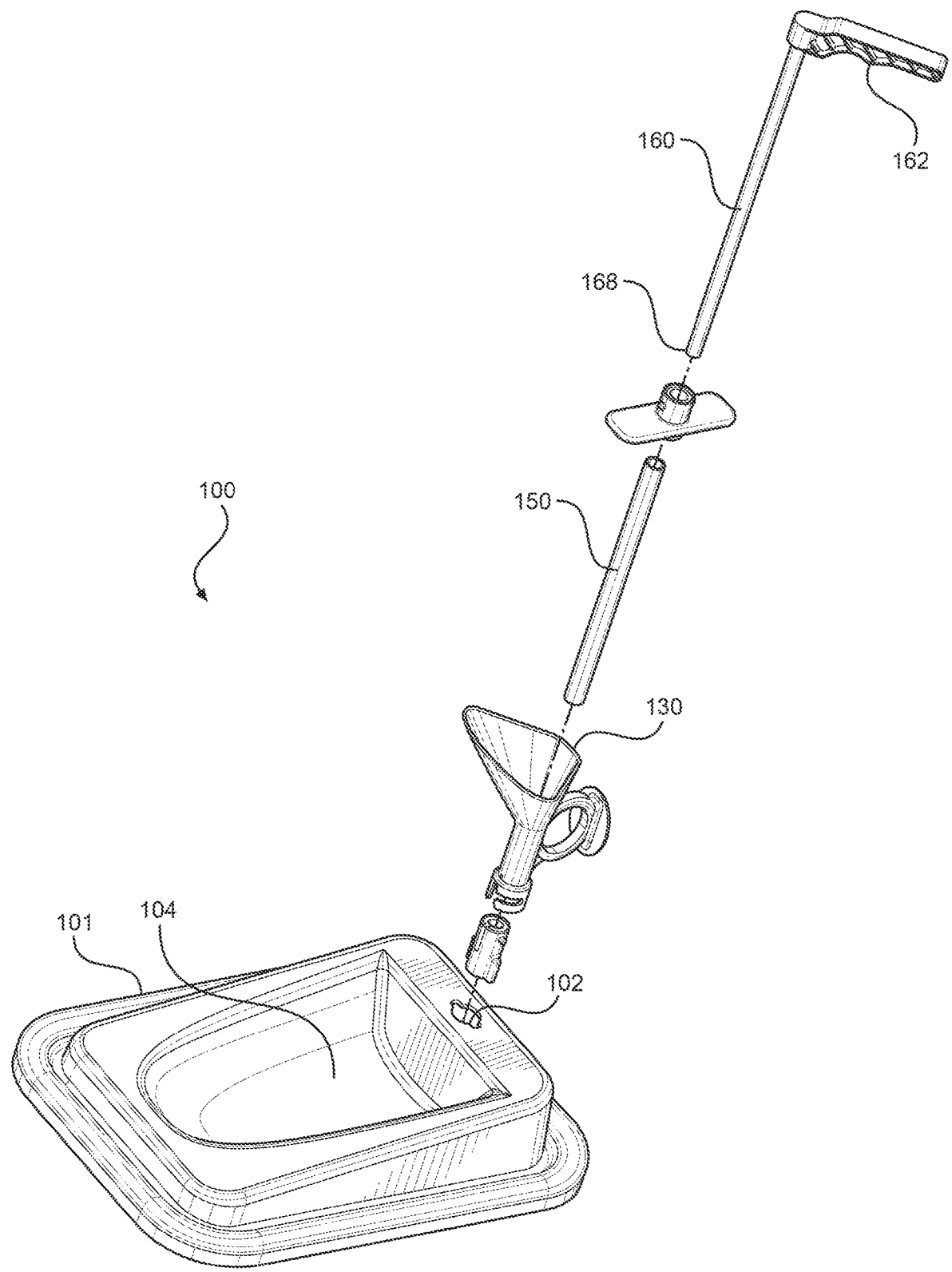
FIG. 2 shows an exploded view of the mixing system shown in FIG. 1.
Figure 3:
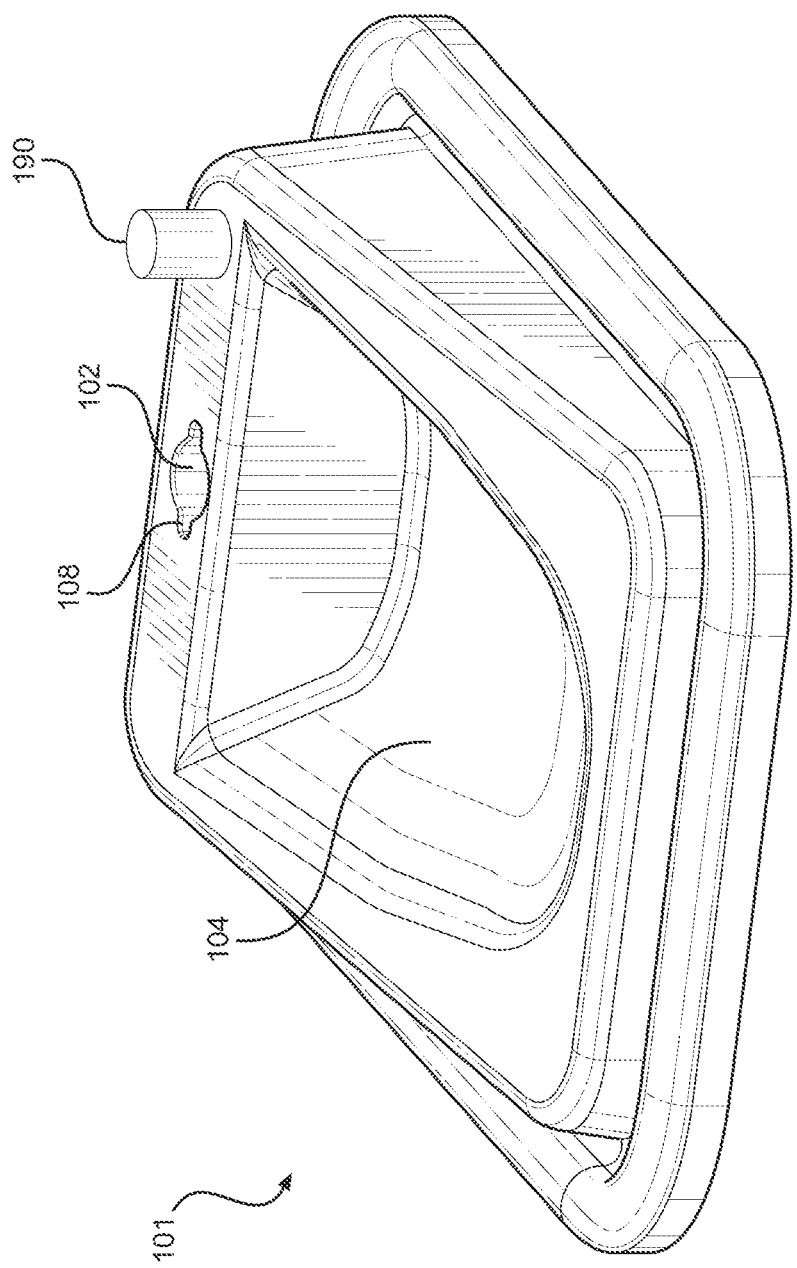
FIG. 3 shows a front isometric view of a tray.

Referring to FIGS. 1-3, the mixing system may include a mixing tray 101, a scooper 130, a tubular member 150, and a stylet 160. A mixing tray 101 defines a mixing receptacle 104 and a connector receptacle 102. The mixing receptacle 104 may be concave. In aspects where a material 10 to be mixed is viscous, the concave shape of the mixing receptacle 104 facilitates mixing and prevents spillage. In some embodiments, the mixing receptacle 104 may define a curved surface, a prismatic surface, or be substantially flat to facilitate cutting, chopping or other manipulation of the material 10. In some embodiments, the mixing receptacle 104 may include separate segments that vary in surface shape and dimension, such that a portion of the mixing receptacle 104 may be flat while another portion of the mixing receptacle 104 may be concave. In some embodiments, the mixing tray 101 may include multiple mixing receptacles 104.

The mixing tray 101 may be made of polyethylene terephthalate (PET), polypropylene, acrylonitrile butadiene styrene (ABS), polyethylene terephthalate glycol-modified (PETG), a combination thereof, or another suitable polymer. In embodiments where the mixing tray is not disposable, it may be made of a metal.

Figure 4A:
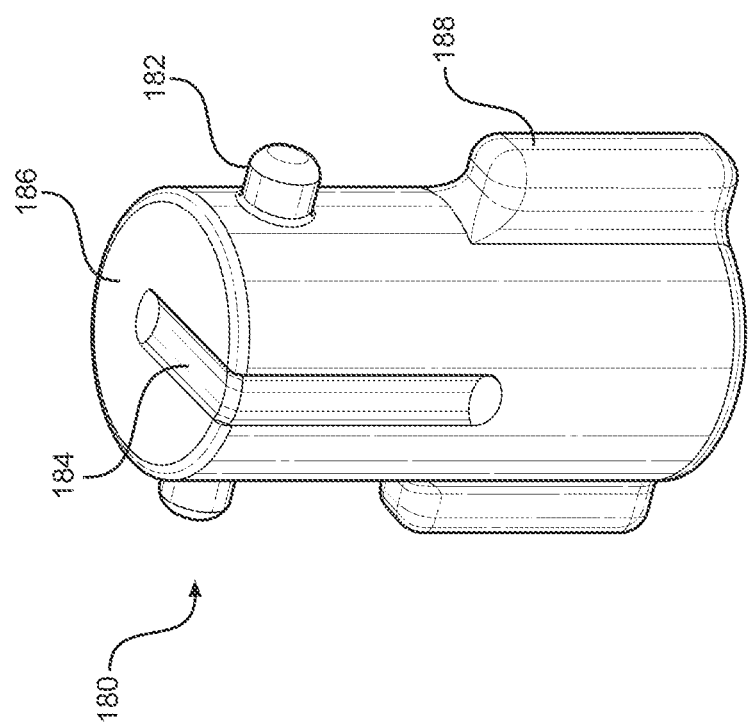
FIGS. 4A-4B show isometric views of a connector.
Figure 4B:
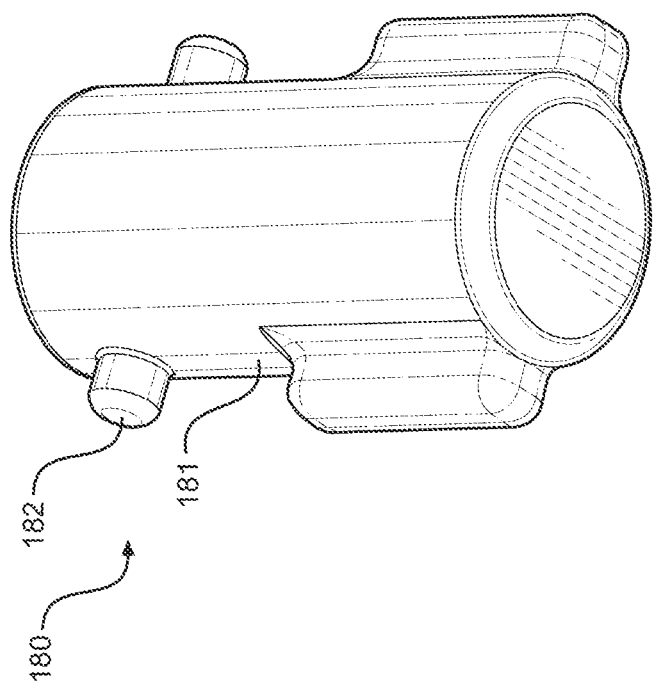
Figure 5:
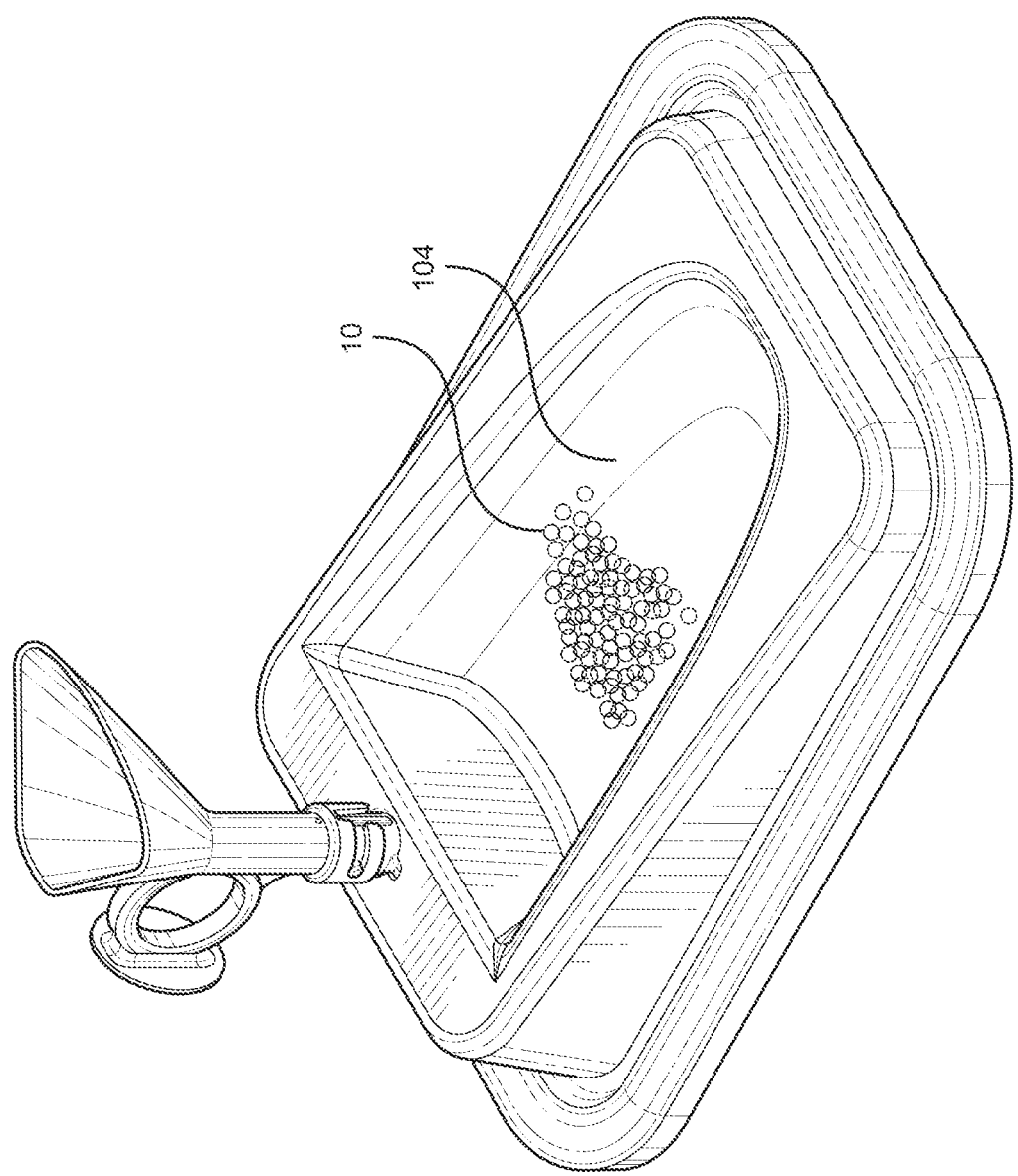
FIG. 5 shows an isometric view of a mixing apparatus with mixed material.
Figure 6:
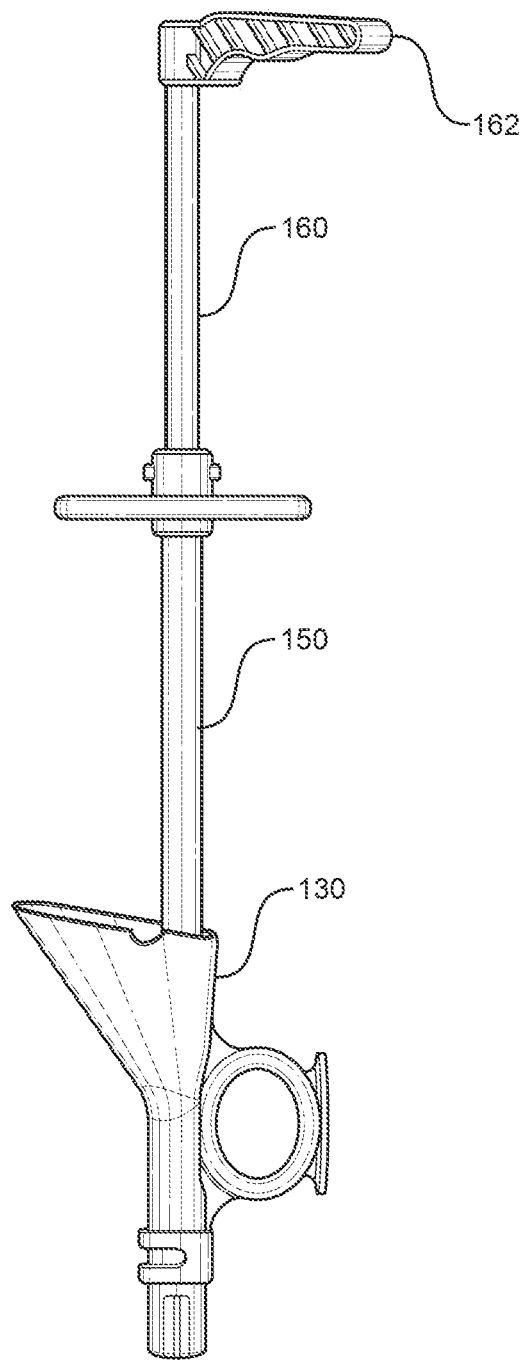
FIG. 6 shows an isometric view of a pushing assembly according to one embodiment.
Figure 7:
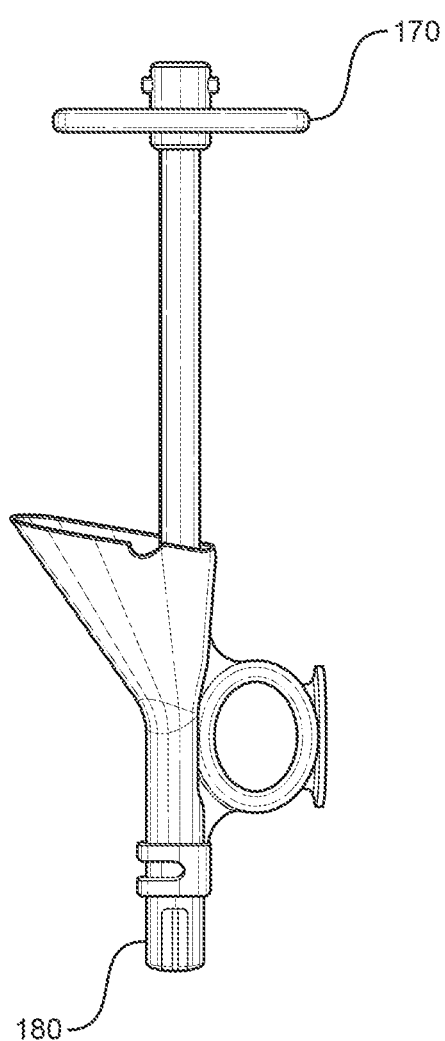
FIG. 7 shows an isometric view of the pushing assembly of FIG. 6 without a stylet.
Figure 9:
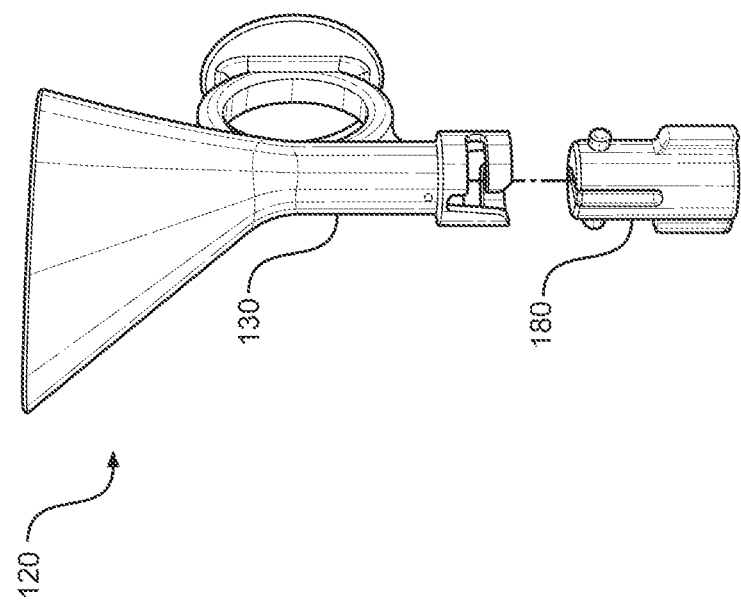
FIG. 9 shows an isometric view of a scooper connection according to another embodiment.
Figure 8:
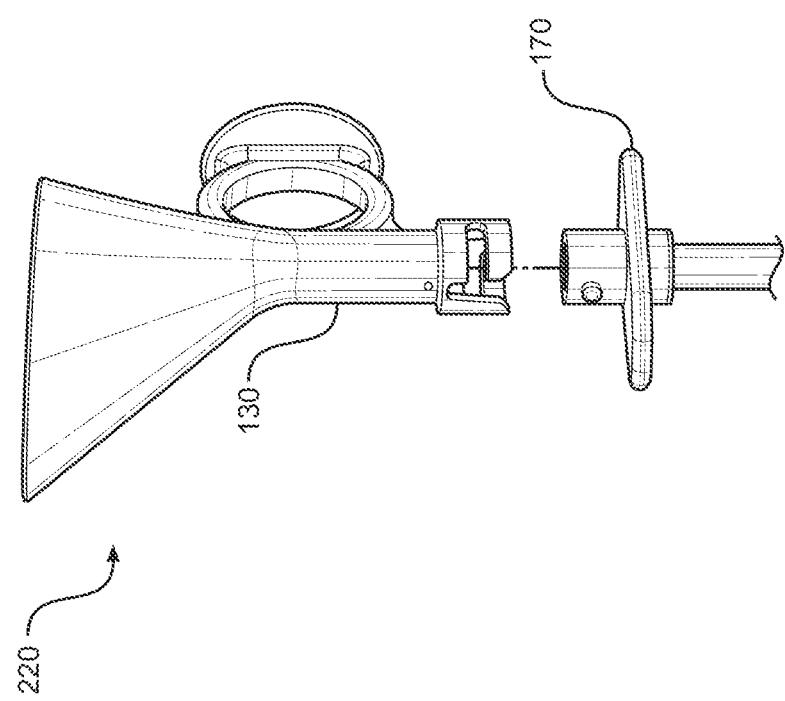
FIG. 8 shows an isometric view of a scooper connection according to one embodiment.
Figure 10:
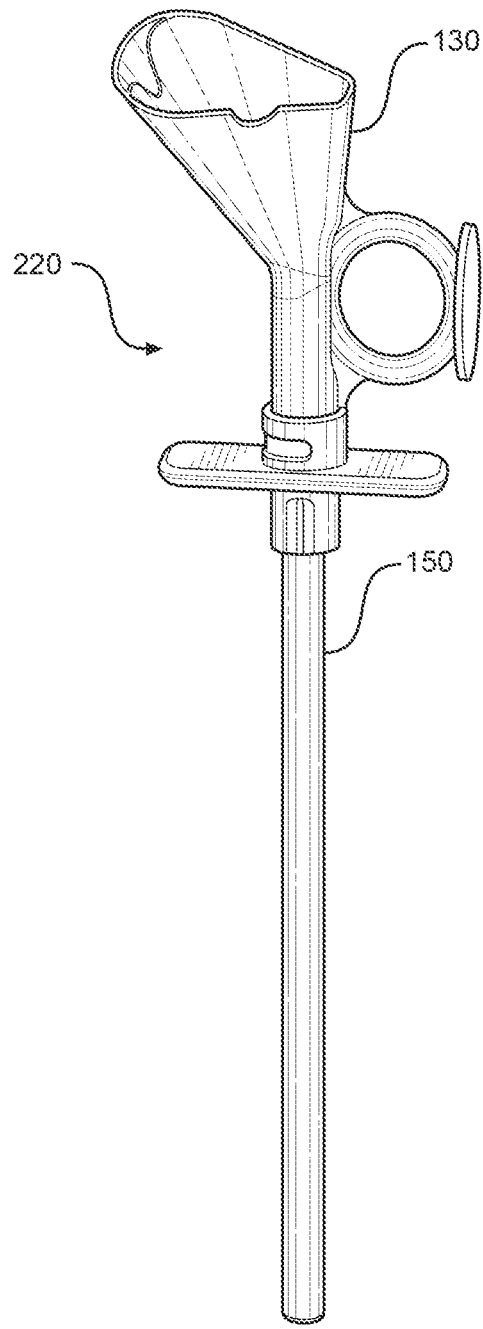
FIG. 10 shows an isometric view of a pushing assembly according to one embodiment.
Figure 11:
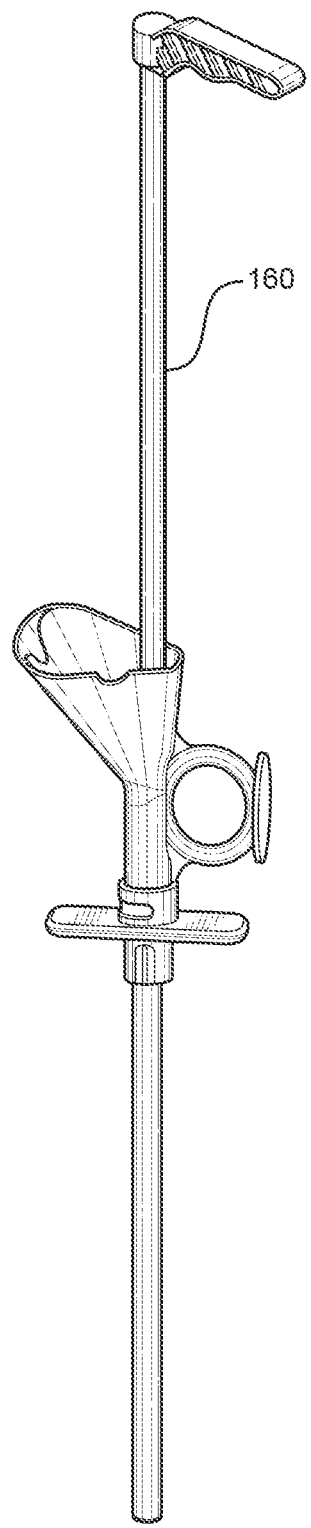
FIG. 11 shows a view of a pushing assembly with a stylet.

The connector receptacle 102 may be sized and shaped to releasably receive a connector 180 or, in some embodiments, the connector 180 may be integral with the mixing tray 101. Referring to FIGS. 3-4B, the connector receptacle 102 may define a channel 108 that is configured to slidably engage with a corresponding tab 188 on the connector 180.

The connector 180 may be releasably secured into the connector receptacle 102 via a friction fit and/or using tabs 188. For example, referring to FIGS. 4A and 4B, the connector 180 includes two tabs 188 that are positioned opposite one another. In addition, the connector 180 may be secured to the mixing tray 101 using glue, screws, or other suitable couplers. In some embodiments, the connector 180 may be made from a material that is more rigid than the mixing tray 101.

The connector 180 can define a channel 184 enabling air or liquid to leave the mixing system 100. In addition, a portion of the material 10 may also move along channel 184 to exit the mixing system 100. In some embodiments, the connector 180 may include a plurality of channels 184 that may be either separately defined or connected to one another.

The connector 180 may include one or more tabs 182 radially extending from the body 181 of the connector 180. The tabs 182 may engage with a scooper 130 to releasably secure the scooper 130 with the connector 180.

Referring to FIGS. 14-18, the scooper 130 has a proximal end 132 defining a proximal opening 133, a distal end 134 defining a distal opening 135, and a passage 136 extending longitudinally there between. The proximal opening 133 may be larger than the distal opening 135. The proximal opening 133 can receive a portion of the material 10 from the mixing tray 101. In some embodiments, the proximal end 132 has the largest cross-sectional area at its proximal-most region and has its smallest cross-sectional area at its distal-most region. The proximal end 132 may function like a funnel so that material 10 introduced into proximal opening 133 may be funneled through the passage 136 into the distal end 134. It will be appreciated that the dimensions of the passage 136 may be such that they accommodate the desired amount of material, and this disclosure is not limited to a particular size or shape of the passage 136 or the volume of desired material 10 to be introduced therein.

Figure 14:
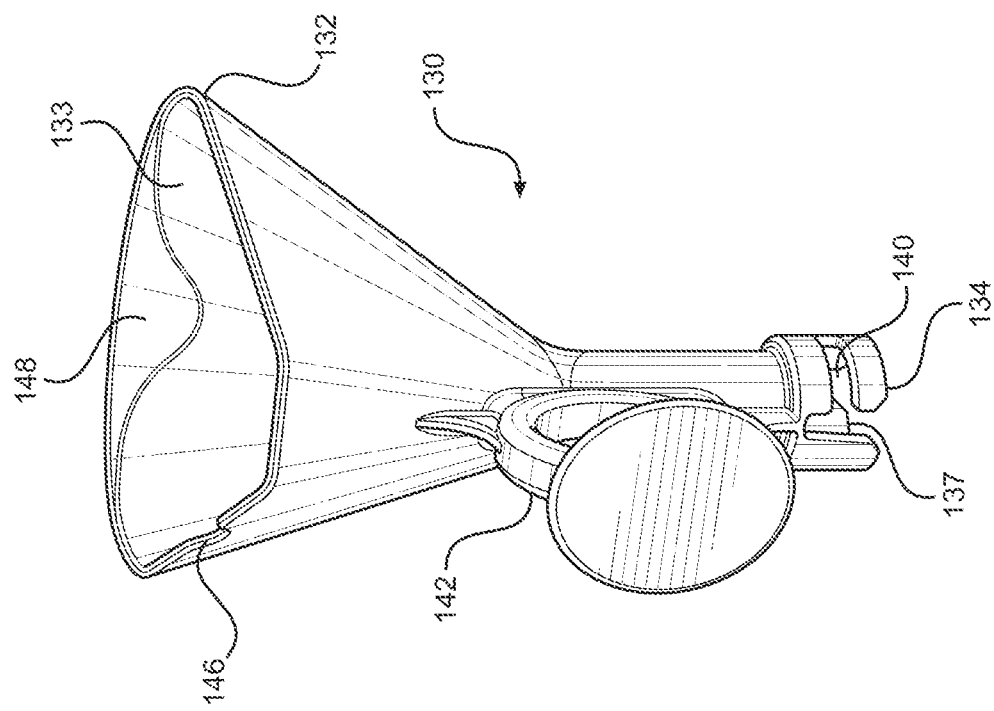
FIG. 14 shows an isometric view of a scooper.
Figure 17:
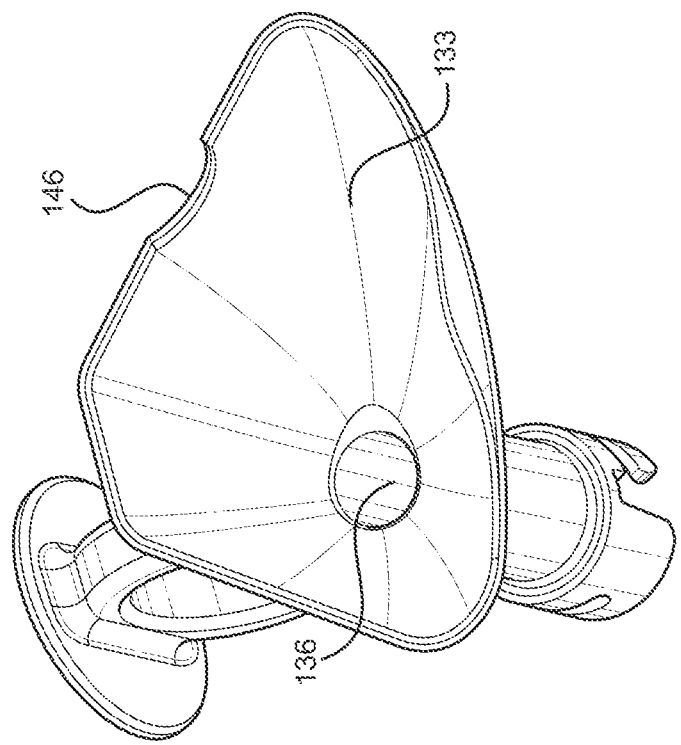
FIG. 17 shows a top isometric view from of the scooper shown in FIGS. 14-16.

The proximal end 132 may include a notch 146 configured to slidably receive the stylet 160 to retain an unused portion of material 10 within the proximal opening 133. In some embodiments, the proximal end 132 may include a tapered edge 148. Referring to FIG. 14, tapered edge 148 is located at the proximal end 132 and is proximally tapered. The tapered edge 148 assists with collecting the material 10 into the scooper 130. In some embodiments, the scooper 130 may include a plurality of tapered edges 148 to receive material from various sides of the proximal end 132. The tapered edge 148 may include an anti-stick coating to reduce friction between the scooper 130 and the material 10.

Figure 16:
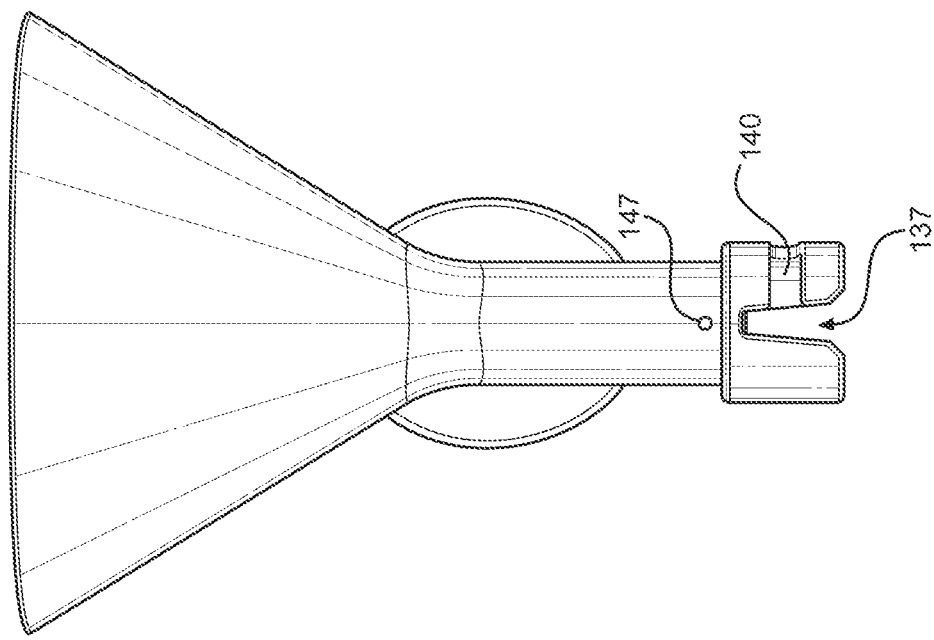
FIG. 16 shows a front perspective view of the scooper shown in FIGS. 14-15.
Figure 18:
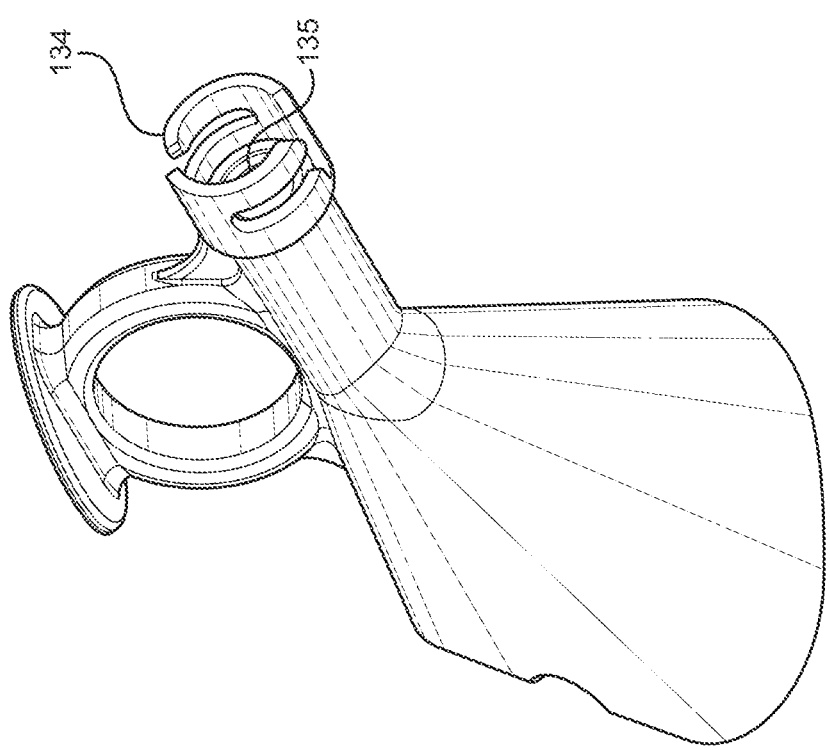
FIG. 18 shows another isometric view of the scooper shown in FIGS. 14-17.

The scooper 130 may further define an aperture 147 to vent air trapped within the material 10 inside the passage 136. The aperture 147 may be located on the proximal end 132 of the scooper 130 or, preferably, on the distal end 134 of the scooper 130. Referring to FIG. 16, the aperture 147 may be substantially round in shape, or have another shape and/or diameter that allow air to pass while preventing the material 10 from passing. In some embodiments, aperture 147 may include a semi-permeable cover (not shown), for example a net or mesh, that allows air to pass while preventing material 10 from passing.

Figure 15:
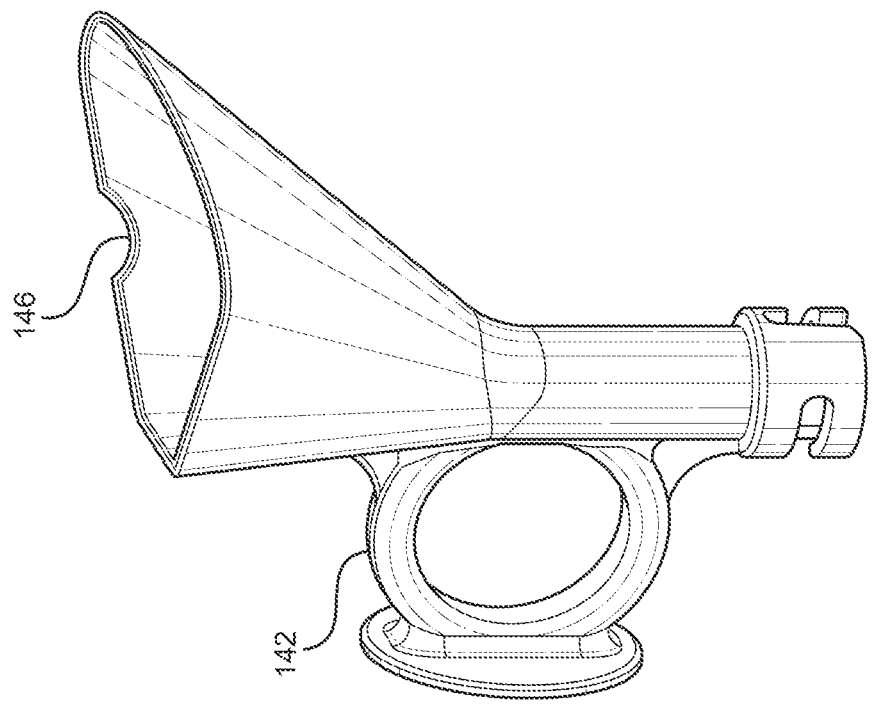
FIG. 15 shows another isometric view of the scooper shown in FIG. 14.

In some embodiments, the scooper 130 may include a grip 142. As shown in FIGS. 14-15, the grip 142 may be ring-shaped, or it may be T-shaped. A user may slide a finger, such as an index finger through an opening in the grip 142 while placing another finger, such as a thumb, on a rest adjacent the opening. Alternatively, the scooper 130 may not include the grip 142 and may be instead grasped by the proximal end 132 or the distal end 134.

Figure 19:
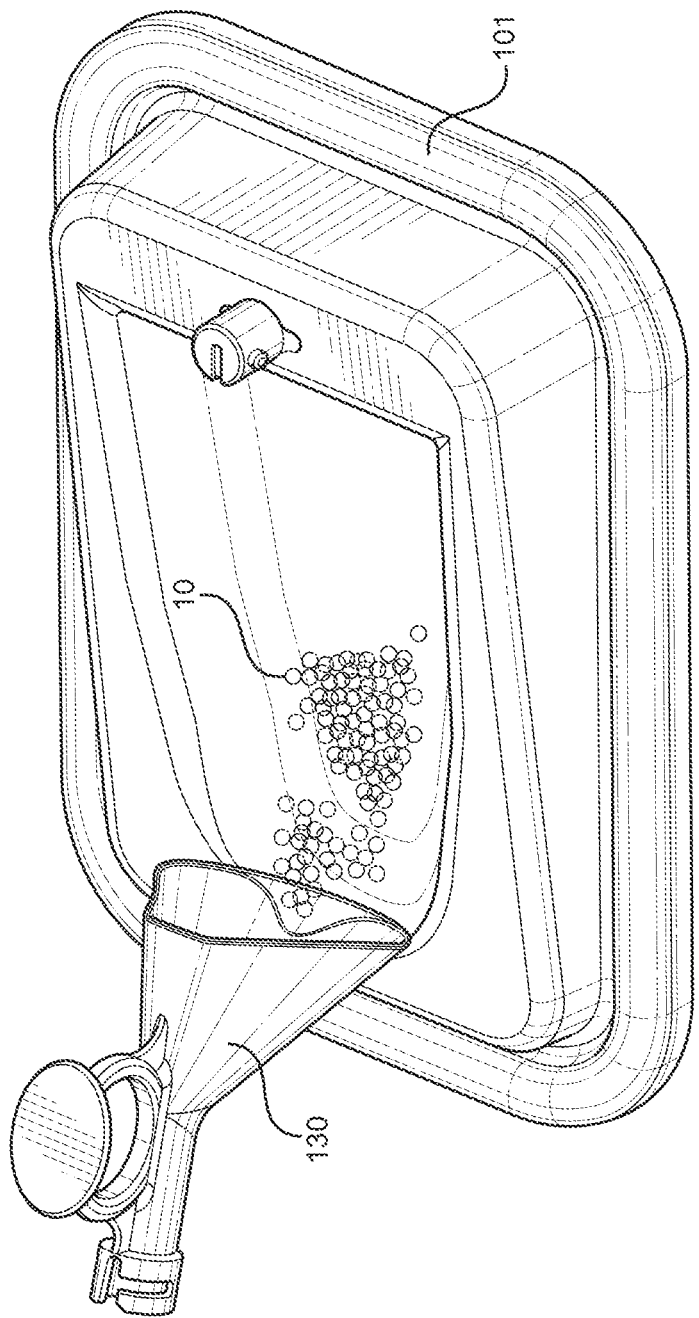
FIG. 19 shows a scooper sliding against the tray according to one embodiment.

The proximal end 132 of scooper 130 is shaped to complement the shape of the mixing receptacle 104 of mixing tray 101 so that the material 10 from the mixing tray 101 may effectively be moved into the scooper 130. The complementary shape of the proximal end 132 maximizes the perimeter of the proximal end 132 that slides against the mixing receptacle 104 to receive the material 10, as shown in FIG. 19.

The scooper 130 may be releasably secured to the connector 180. For example, the scooper 130 may include a groove 140 at the distal end 134 that receives the tab 182 on the connector 180. The tab 182 may pass into a cavity 137 and then into the groove 140 upon relative rotation of the scooper 130 and the connector 180 to releasably secure the scooper 130 to the connector 180. As such, when the connector 180 is connected to the mixing tray 101, the scooper 130 is also removably attached to the mixing tray 101 by virtue of its attachment to connector 180. When the scooper 130 is connected to the connector 180, translational movement of the scooper 130 relative to the connector 180 is inhibited. In some embodiments, the distal end 134 of the scooper 130 may rotate independent of the rest of scooper 130, and in such embodiments, it may be sufficient to only rotate the distal end 134 to slide the groove 140 over the tab 182. Two tabs 182 are shown in FIGS. 4A-4B and, therefore, scooper 130 includes two grooves 140 in FIG. 18.

In some embodiments, the groove 140 may not include the cavity 137, such that the groove 140 has a closed circumference. In such embodiments, the tab 182 may have a variable protrusion length so it can retract to be received within the distal opening 135 and resiliently extend to be received within the groove 140. For example, the tab 182 may include a spring to resiliently extend the tab 182.

Figure 13A:
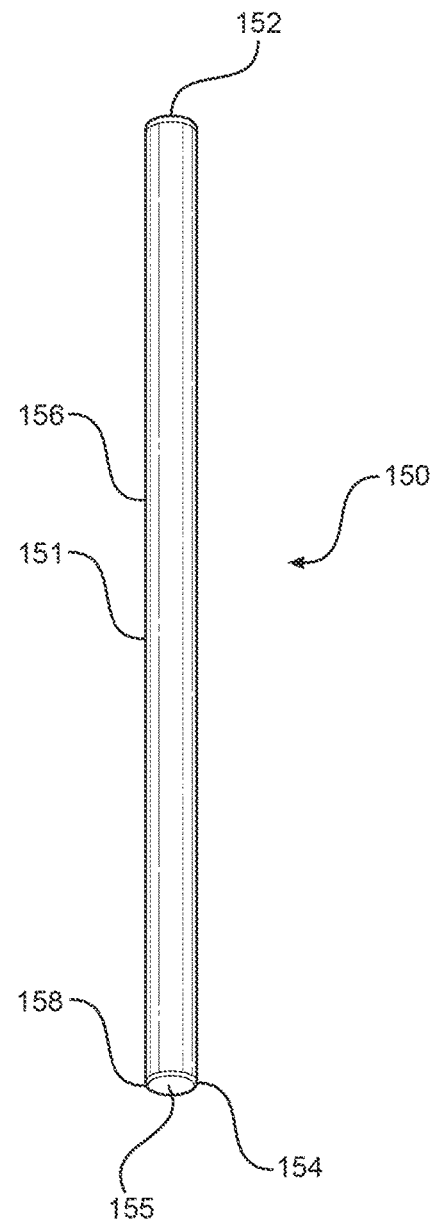
FIG. 13A shows an isometric view of a tubular member.

The mixing system 100 may also include the tubular member 150. Referring to FIG. 13A, the tubular member 150 has a tubular body 151, a proximal end 152 having proximal opening 153, and a distal end 154 having distal opening 155. The tubular body 151 defines a lumen 156 extending through the tubular body 151 between the proximal opening 153 and the distal opening 155. The lumen 156 is sized to receive the material 10. The tubular member 150 has an outer diameter that is smaller than the inner diameter of the scooper passage 136, such that tubular member 150 can pass into the passage 136.

The tubular member 150 may include markings (not shown) on the tubular body 151. The markings may include measurements, material information, dates, or other information. The markings may be printed, they may be protrusions, or they may be notches on the tubular body 151. In some embodiments, the markings may be radio-opaque such that they are readily observable under X-ray or other radiation. The tubular member 150 may be at least partially translucent. As such, a user can visualize the amount of material inside the lumen 156 under radiation.

In some embodiments, the distal end of the tubular member 150 may releasably secure to other devices, such as a syringe or another tubular member 150. The tubular member 150 may include a closure cap (not shown) configured to removably attached to the proximal end 152, the distal end 154, or both ends. In some embodiments, distal end 154 of tubular member 150 may beveled to guide the material 10 entering the tubular member towards the center of the lumen 156.

The tubular member 150 may also include a handle 170. In some embodiments, proximal end 174 may define a proximal opening 175, and distal end 176 may define a distal opening 177. The body 171 may further define a lumen extending between proximal opening 175 and distal opening 177. In some embodiments, the handle 170 includes a distal opening 177 but not a proximal opening. Distal opening 177 of handle 170 may be sized to receive the proximal end 152 of tubular member 150. Tubular member 150 may be wedgedly secured to handle 170. Alternatively, or additionally, tubular member 150 may be fastened to handle 170 with glue, screws, clips, or other suitable fasteners. In some embodiments, the tubular member 150 and the handle 170 may be a unitary piece.

Referring to FIG. 3, the mixing tray 101 may include an attachment post 190 configured to receive the tubular member 150 at the distal end 154. The attachment post 190 may be shaped and dimensioned such that it has clearance to pass into the distal opening 155 such that the tubular member 150 is removably secured to the mixing tray 101 via the attachment post 190. The tubular member 150 may be secured to the attachment post 190 by any suitable method, for example, by threaded engagement, snap fit, interference fit, or another suitable method of securing the tubular member 150 to the attachment post 190. The attachment post 190 may be dimensioned such that it has enough clearance to pass into the distal opening 155, but not so much clearance that the tubular member 150 is unsecured (e.g. wobbles or slides off the attachment post 190).

Securing the tubular member 150 to the attachment post 190 allows the user to introduce material into the tubular member 150 without having to also hold the tubular member 150. Additionally, the mixing tray 101 acts as a base to prevent the tubular member 150 from falling or tipping, which decreases the chance of spilling the material and/or contaminating the surrounding environment. The attachment post 190 may also provide a rigid floor to the tubular member 150 at the distal end 154 to allow the material to be compacted properly and to avoid under-filling or formation of air pockets within the material in the tubular member 150.

In some embodiments, the attachment post 190 may be dimensioned such that it may receive the distal end 154 rather than be received into the distal opening 155. In such embodiments, the attachment post 190 may have an opening (not shown) into which the tubular member 150 may be inserted and secured via one of the methods described above.

While the attachment post 190 and the connector 180 are described as individual components, it will be understood that in some embodiments, the two components may be interchangeable, and the mixing system 100 may include one or more of the connectors 180 or attachment posts 190. In some embodiments, for example, only one component (either the connector 180 or the attachment post 190) may be present and serve the role of both as described herein.

Figure 13B:
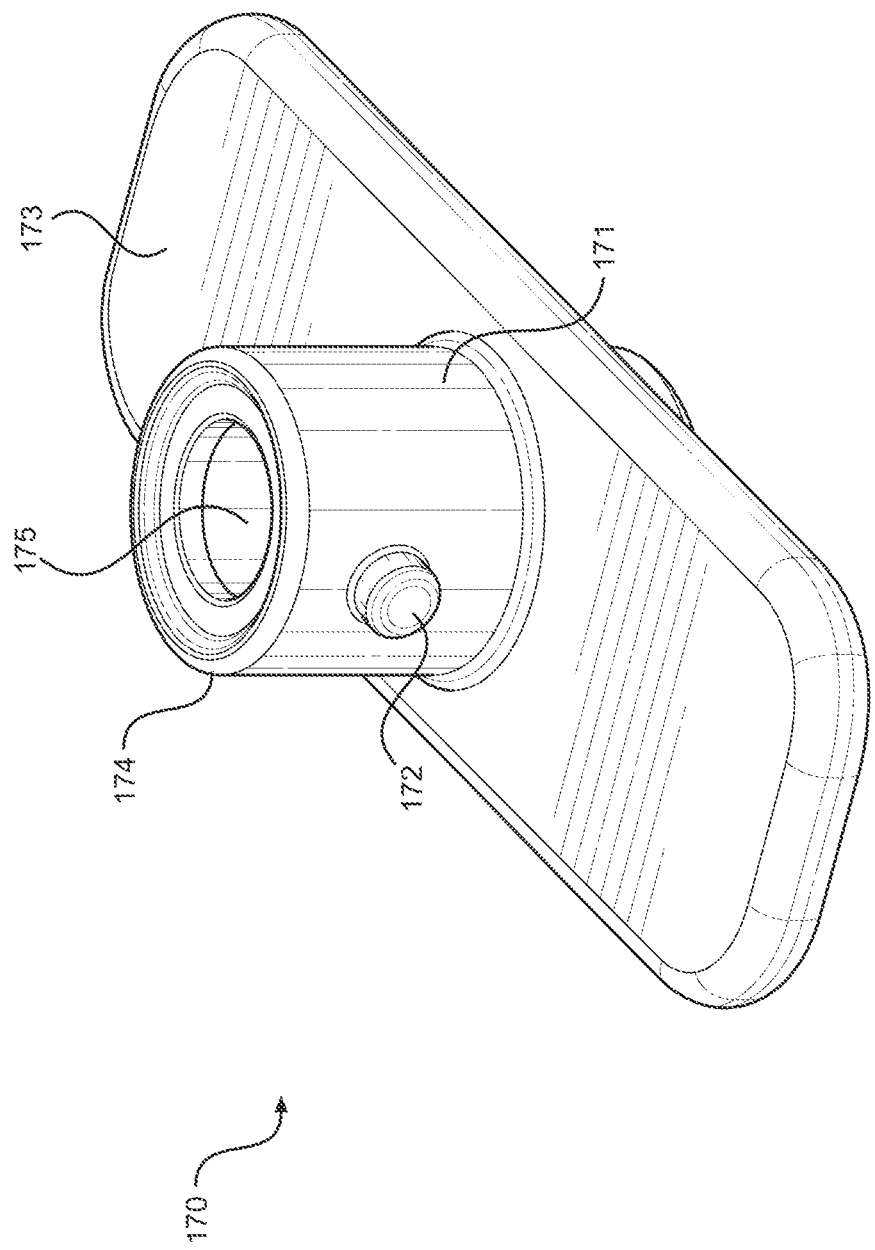
FIG. 13B shows an isometric view of a tubular member handle.

Referring to FIGS. 13B-C, in some embodiments, the handle 170 may include a tab 172 or a plurality of tabs 172, such as two tabs 172 opposite one other on the body 171. The tabs 172 may be substantially similar in size, shape, and function as tabs 182 described above in connection with the connector 180. The tabs 172 may engage with the distal end 134 of scooper 130, similar to the engagement of the tabs 182.

When the scooper 130 is removably secured to the handle 170 of the tubular member 150, the proximal opening 175 of handle 170 may be in fluid communication the distal opening 135 of the scooper 130 such that material 10 within the scooper 130 may pass from the distal opening 135 into the proximal opening 175 of the handle 170.

The mixing system 100 may also include the stylet 160. Referring to FIG. 2, the stylet 160 may include a stylet handle 162 configured to be received within the hand of the user. The stylet handle 162 may define regions to receive a plurality of the user's fingers. The stylet 160 has an outer diameter that is smaller than an inner diameter of the lumen 156 of the tubular member 150 and the passage 136 of the scooper 130. As such, the stylet 160 may pass through the lumen 156 or the passage 136. The stylet 160 can be used as a plunger to push material through the tubular member 150 or the scooper 130.

The stylet 160 may be sloped or tapered at its distal end 168. The slope or taper may be angled such that when the distal end 168 contacts the material in the tubular member 150 or in the scooper 130, the material is pushed farther in the direction of movement of the stylet 160. In some embodiments, the distal end 168 may be concave, such that the material is pushed towards the centerline of the stylet 160 as the stylet 160 is moved axially in the tubular member 150 or the scooper 130. In an alternative embodiment, the distal end 168 may be convex, such that the material is pushed away from the centerline of the stylet 160. Various advantages may exist for different stylet shapes, such as increased precision when dispensing material, better spreading of the material within the tubular member 150 and/or the scooper 130, and reduced clogging of the material inside the components of the mixing system 100.

The stylet 160 may include markings (not shown) to indicate measurements, material information, or part reference numbers. The markings may be printed, protrusions or notches, and may be radio-opaque. In some embodiments, therefore, as the stylet 160 passes through the lumen 156 of the tubular member 150, the markings on the distal end 168 of stylet 160 can be observed relative to the radio-opaque markings on the tubular body 151.

The components of mixing system 100 may all be manufactured from the same material, or alternatively, may comprise different materials. Manufacturing materials may comprise plastic or metal, or a combination of plastic or metal. Materials used may include polyethylene terephthalate (PET), polyethylene terephthalate glycol-modified (PETG), polypropylene, acrylonitrile butadiene styrene (ABS), or another suitable polymer. In some embodiments, combinations of materials may be used. Some embodiments may comprise materials that are at least partly translucent. The materials may be suitable for sterilization via autoclaving, ethylene oxide exposure, gamma ray radiation, or another suitable method of sterilization that can be used in the medical field. A portion of the mixing system or the entire system itself may be designed to be reusable. Alternatively, a portion of the system or the entire system may be disposable.

In use, after the material 10 is prepared and/or mixed within the mixing receptacle 104 of mixing tray 101, the material 10 may be moved into scooper 130. As shown in FIG. 19, the proximal end 132 of the scooper 130 is positioned adjacent the mixing receptacle 104. The scooper 130 may be moved along the surface of the mixing receptacle 104 such that material is transferred from the mixing receptacle into proximal opening 133. The material 10 may be similarly moved into the proximal end 132 by an external tool (not shown) that urges the material 10 from the mixing receptacle 104 into the scooper 130.

After a sufficient amount of the material 10 has been moved into the scooper 130, the scooper 130 may be removably attached to the connector 180, as described above, where the connector 180 is already attached to the mixing tray 101. The tubular member 150 may then be introduced into the proximal opening 133 of scooper 130 and moved in a distal direction to receive the material 10 within its lumen 156. When a sufficient amount of the material 10 is transferred into the tubular member 150, the tubular member 150 may be detached from the connector 180 and introduced to a surgical site. The stylet 160 may be introduced into the proximal opening 153 of the tubular member 150 and moved distally through the lumen 156 to move a portion of the material 10 into the surgical site through the distal opening 155 of the tubular member 150.

Figure 12:
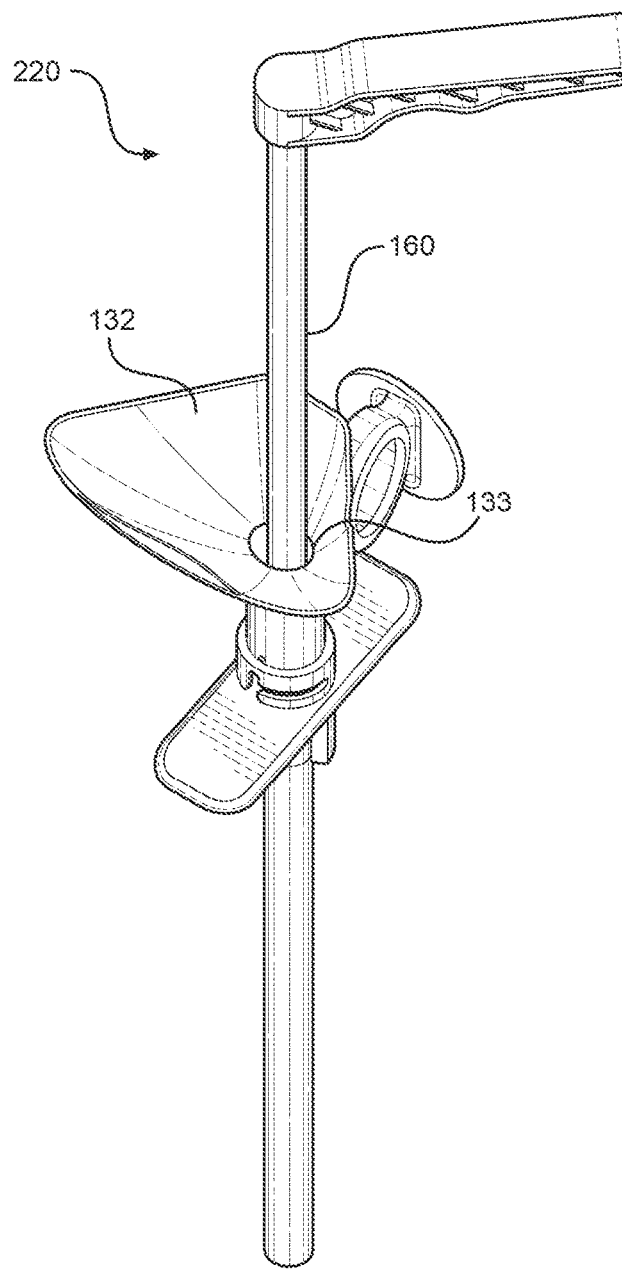
FIG. 12 shows an isometric view of the pushing assembly in FIG. 11.

Referring to FIG. 12, in some embodiments where the distal end of the scooper 130 is removably attached to the handle 170 of the tubular member 150 as opposed to the connector 180, the stylet 160 may be used to push the material 10 out of the distal opening 135 of the scooper 130 into the lumen 156 of tubular member 150.

In the present disclosure the singular forms "a," "an," and "the" include the plural reference and reference to a particular numerical value includes at least that particular value, unless the context clearly indicates otherwise. Thus, for example, a reference to "a material" is a reference to at least one of such materials and equivalents thereof known to those skilled in the art, and so forth.

It is to be understood that this disclosure is not limited to the specific devices, methods, conditions or parameters described or shown herein, and that the terminology used herein is for the purpose of describing particular embodiments by way of example only and is not intended to be limiting of any subject matter claimed.

What is claimed is:

1. A method of preparing a medical mixture, the method comprising:
    introducing a material into a tray;
    transferring the material from the tray to a scooper;
    releasably securing the scooper to the tray; and
    introducing a tubular member defining a lumen into the scooper such that the material within the scooper enters the lumen.
2. The method of claim 1, wherein introducing the material comprises introducing a first material and a second material, wherein the first material is different from the second material.
3. The method of claim 2, wherein the first material comprises natural bone and the second material comprises synthetic material.
4. The method of claim 2, further comprising mixing the first material and the second material in the tray.
5. The method of claim 1, wherein introducing the material into the tray comprises introducing the material in a mixing receptacle defined by the tray.
6. The method of claim 5, wherein releasably securing the scooper to the tray comprises releasably securing the scooper to a position on the tray adjacent the mixing receptacle.
7. The method of claim 1, wherein releasably securing the scooper to the tray comprises sliding a distal end of the scooper over a post extending from the tray.
8. A method of preparing a medical mixture, the method comprising:
    introducing a material into a tray;
    transferring the material from the tray to a scooper having a distal opening at a distal end and a proximal opening at a proximal end, such that the material is transferred to the scooper through the proximal opening; and
    releasably securing the scooper to a tubular member, the tubular member having a proximal opening at a proximal end and a distal opening at a distal end and defining a lumen that extends from the proximal opening to the distal opening,
    wherein the distal end of the scooper is releasably secured to the proximal end of the tubular member such that the distal opening of the scooper is in fluid communication with the proximal opening of the tubular member.
9. The method of claim 8, further comprising moving a stylet into the proximal opening of the scooper to push at least some of the material from the scooper into the lumen of the tubular member.
10. The method of claim 8, wherein introducing the material into the tray comprises introducing the material in a mixing receptacle defined by the tray.
11. The method of claim 8, wherein introducing the material comprises introducing a first material and a second material, wherein the first material is different from the second material.
12. The method of claim 11, wherein the first material comprises natural bone and the second material comprises synthetic material.
13. The method of claim 11, further comprising mixing the first material and the second material in the tray.

* * * * *